(12) United States Patent
Chen et al.

(10) Patent No.: US 11,857,536 B2
(45) Date of Patent: Jan. 2, 2024

(54) GLUCOKINASE ACTIVATOR FOR TREATING DIABETES WITH RENAL IMPAIRMENT

(71) Applicant: HUA Medicine (Shanghai) Ltd., Shanghai (CN)

(72) Inventors: Li Chen, Shanghai (CN); Shuang Ren, Shanghai (CN); Chengfeng Jiao, Shanghai (CN); Yaohui Wang, Beijing (CN)

(73) Assignee: HUA Medicine (Shanghai) Ltd., Shanghai (CN)

( * ) Notice: Subject to any disclaimer, the term of this patent is extended or adjusted under 35 U.S.C. 154(b) by 65 days.

(21) Appl. No.: 17/338,555

(22) Filed: Jun. 3, 2021

(65) Prior Publication Data

US 2021/0379019 A1    Dec. 9, 2021

Related U.S. Application Data

(60) Provisional application No. 63/034,624, filed on Jun. 4, 2020.

(51) Int. Cl.
| | |
|---|---|
| *A61K 31/4155* | (2006.01) |
| *A61K 45/06* | (2006.01) |
| *A61K 9/20* | (2006.01) |
| *A61K 9/00* | (2006.01) |

(52) U.S. Cl.
CPC .......... *A61K 31/4155* (2013.01); *A61K 45/06* (2013.01); *A61K 9/0053* (2013.01); *A61K 9/20* (2013.01)

(58) Field of Classification Search
CPC ................................................. A61K 31/4155
See application file for complete search history.

(56) References Cited

U.S. PATENT DOCUMENTS

| | | | |
|---|---|---|---|
| 7,812,048 B2 * | 10/2010 | Shi ...................... | C07D 513/04 514/400 |
| 11,266,630 B2 * | 3/2022 | Chen .................... | A61K 9/1635 |
| 2019/0328713 A1 * | 10/2019 | Chen ................... | A61K 31/4439 |
| 2021/0196682 A1 | 7/2021 | Chen et al. | |
| 2021/0196683 A1 | 7/2021 | Chen et al. | |
| 2021/0214343 A1 | 7/2021 | Chen et al. | |
| 2021/0220334 A1 | 7/2021 | Chen et al. | |

FOREIGN PATENT DOCUMENTS

| | | |
|---|---|---|
| EP | 3556354 A1 | 10/2019 |
| WO | WO 2013/173417 A2 | 11/2013 |
| WO | WO 2014/137797 A2 | 9/2014 |
| WO | WO 2019/228362 A1 | 12/2019 |
| WO | WO 2019/228363 A1 | 12/2019 |
| WO | WO 2019/228364 A1 | 12/2019 |
| WO | WO 2019/228365 A1 | 12/2019 |

OTHER PUBLICATIONS

NCT04324424: A Clinical Study to Access the Pharmacokinetics of HMS5552 in Renal Impaired Subjects and Healthy Volunteers, First Posted Mar. 27, 2021, downloaded Jul. 30, 2021 from internet: https://clinicaltrials.gov/ct2/show/NCT04324424.
Hua Medicine, "Hua Medicine—Business & Pipeline Update", press release dated Jun. 5, 2019.

* cited by examiner

*Primary Examiner* — Rei Tsang Shiao
(74) *Attorney, Agent, or Firm* — Jones Day

(57) ABSTRACT

Provided herein is a method of treating, preventing, or ameliorating one or more symptoms of a glucokinase-mediated disorder, disease, or condition in a renally impaired subject with a glucokinase activator (GKA), for example, dorzagliatin. Also provided herein is a method of treating, preventing, or ameliorating one or more symptoms of a diabetes in a renally impaired subject with a GKA. Additionally, provided herein is a method of treating, preventing, or ameliorating one or more symptoms of a chronic kidney disease with a GKA.

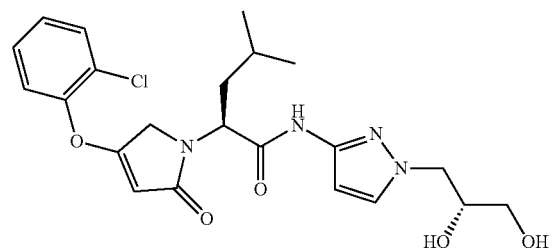

45 Claims, 1 Drawing Sheet

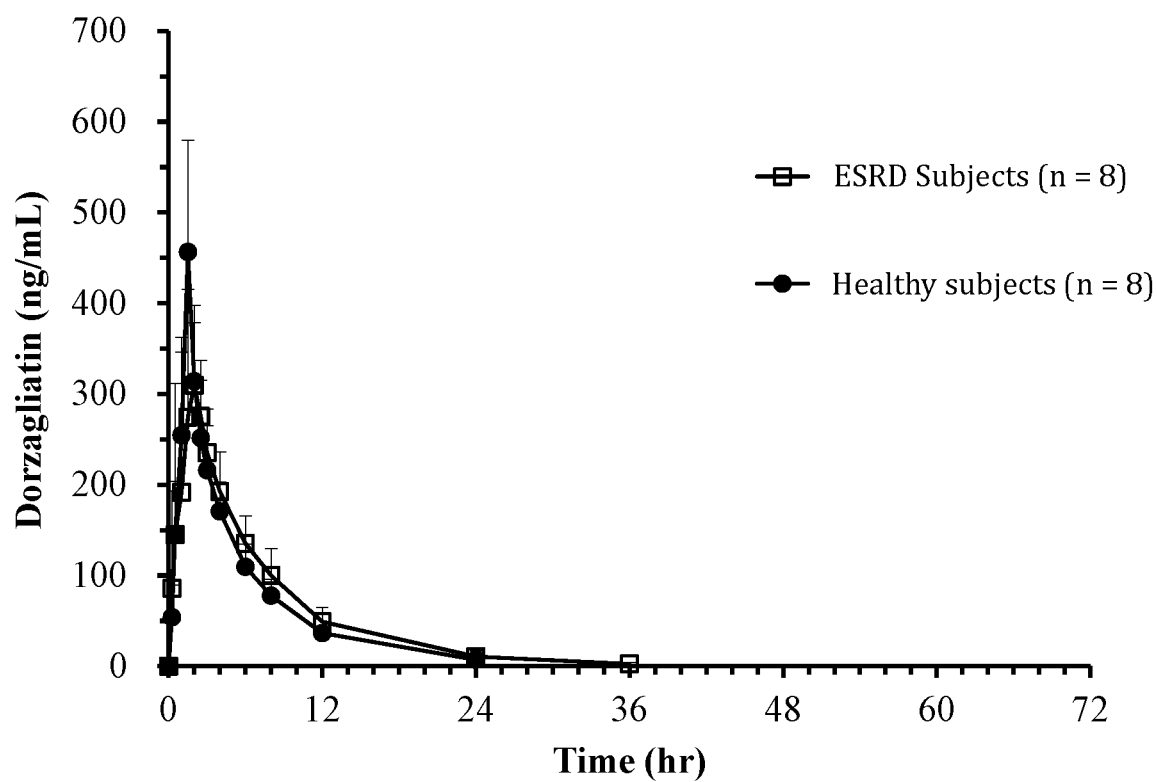

GLUCOKINASE ACTIVATOR FOR TREATING DIABETES WITH RENAL IMPAIRMENT

CROSS-REFERENCE TO RELATED APPLICATIONS

This application claims the benefit of U.S. Provisional Application No. 63/034,624, filed Jun. 4, 2020, the entirety of which is incorporated herein by reference.

FIELD

Provided herein is a method of treating, preventing, or ameliorating one or more symptoms of a glucokinase-mediated disorder, disease, or condition in a renally impaired subject with a glucokinase activator (GKA). Also provided herein is a method of treating, preventing, or ameliorating one or more symptoms of a diabetes in a renally impaired subject with a GKA. Additionally, provided herein is a method of treating, preventing, or ameliorating one or more symptoms of a chronic kidney disease with a GKA.

BACKGROUND

Diabetes mellitus is a major health issue in the world. Nearly half a billion people are living with diabetes worldwide in 2019. *IDF Diabetes Atlas;* 9th ed.; International Diabetes Federation; 2019. Type 2 diabetes (T2DM), a non-insulin dependent diabetes mellitus, accounts for more than 90% of diabetes in the world. Id.; Wu et al., *Int. J Med. Sci.* 2014, 11, 1185-1200. Diabetes mellitus is also the leading cause of a chronic kidney disease (CKD). National Kidney Foundation, *Am J. Kidney Dis.* 2012, 60, 850-886. Approximately 20-30% of T2DM patients have renal impairment, classified as a moderate-to-severe CKD with a glomerular filtration rate (GFR) less than 60 mL/min/1.73 $m^2$. Huang et al., *Diabetes Care* 2011, 34, 1329-1336. As the prevalence of T2DM continues to increase rapidly worldwide, it is almost certain that the proportion of CKD attributable to T2DM will continue to rise. National Kidney Foundation, *Am J. Kidney Dis.* 2012, 60, 850-886; Wu et al., *Int. J. Med. Sci.* 2014, 11, 1185-1200. Unfortunately, the combination of diabetes and CKD is associated with increased morbidity and mortality. Grandfils et al., *Int. J Endocrinol.* 2013, 2013, 640632.

Glucokinase (GK) plays a central role in stabilizing the blood glucose balance in the human body. GK as a glucose sensor in glucose homeostasis, regulates the secretion of glucagon, insulin, and GLP-1 stimulated by glucose. GK is mainly distributed in the liver, where it rapidly converts glucose into hepatic glycogen for storage in response to elevated blood glucose and meanwhile lowers the glucose level in the blood. A defect of glucokinase causes impaired glucose tolerance (IGT) and type 2 diabetes. However, there is currently no GKAs approved for clinical use.

The hyperglycemia, the defining feature of diabetes, is a fundamental cause of vascular target organ complications, including a diabetic kidney disease (DKD). National Kidney Foundation, *Am J. Kidney Dis.* 2012, 60, 850-886. However, the management of hyperglycemia in patients with a CKD is especially difficult because of treatment complexity and associated risks, such as severe hypoglycemia. Carolina et al., *Clinics* 2016, 71, 47-53. The decline in renal function can impair the clearance and metabolism of an antidiabetic agent. Id. As a consequence, many antidiabetic agents are not recommended or require dose adjustment for treating renally impaired diabetic patients. Id.; National Kidney Foundation, *Am J. Kidney Dis.* 2012, 60, 850-886. For example, metformin, generally the first medication prescribed for T2DM, is contraindicated for diabetic patients with severe renal impairment with a GFR below 30 mL/min/1.73 $m^2$, and not recommended for diabetic patients with a GFR between 30 and 45 mL/min/1.73 $m^2$. GLUCOPHAGE® and GLUCOPHASE® XR Prescription Label (May 2018).

Therefore, there is a clinical need to be met in treating a diabetes with renal impairment.

SUMMARY OF THE DISCLOSURE

Provided herein is a method of treating, preventing, or ameliorating one or more symptoms of a glucokinase-mediated disorder, disease, or condition in a subject with renal impairment, comprising administering to the subject in need thereof a therapeutically effective amount of a glucokinase activator (GKA).

Also provided herein is a method of treating, preventing, or ameliorating one or more symptoms of a diabetes in a subject with renal impairment, comprising administering to the subject in need thereof a therapeutically effective amount of a GKA.

Additionally, provided herein is a method of treating hyperglycemia in a subject with renal impairment, comprising administering to the subject in need thereof a therapeutically effective amount of a GKA.

Furthermore, provided herein is a method of treating prediabetes in a subject with renal impairment, comprising administering to the subject in need thereof a therapeutically effective amount of a GKA.

Provided herein is a method of treating, preventing, or ameliorating one or more symptoms of a chronic kidney disease in a subject, comprising administering to the subject in need thereof a therapeutically effective amount of a GKA.

Provided herein is a method of slowing the progression of a chronic kidney disease to end-stage renal disease (i.e., kidney failure) in a subject, comprising administering to a subject in need thereof a therapeutically effective amount of a GKA.

Provided herein is a method of modulating the activity of a glucokinase in a subject with renal impairment, comprising administering to the subject in need thereof an effective amount of a GKA.

Provided herein is a method of treating, preventing, or ameliorating one or more symptoms of diabetes in a subject with renal impairment, comprising administering to the subject in need thereof a therapeutically effective amount of (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide, or a tautomer, a mixture of two or more tautomers, or an isotopic variant thereof; or a pharmaceutically acceptable salt, solvate, hydrate, or prodrug thereof.

Provided herein is a method of treating, preventing, or ameliorating one or more symptoms of a chronic kidney disease in a subject, comprising administering to the subject in need thereof a therapeutically effective amount of (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide, or a tautomer, a mixture of two or more tautomers, or an isotopic variant thereof; or a pharmaceutically acceptable salt, solvate, hydrate, or prodrug thereof.

BRIEF DESCRIPTION OF THE DRAWINGS

FIG. 1 depicts the pharmacokinetic profiles of dorzagliatin (25 mg) after a single oral dose in subjects with normal and impaired renal functions.

DETAILED DESCRIPTION

To facilitate understanding of the disclosure set forth herein, a number of terms are defined below.

Generally, the nomenclature used herein and the laboratory procedures in organic chemistry, medicinal chemistry, biochemistry, biology, and pharmacology described herein are those well-known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "therapeutically effective amount" or "effective amount" is meant to include the amount of a compound that, when administered, is sufficient to prevent development of, or alleviate to some extent, one or more of the symptoms of the disorder, disease, or condition being treated. The term "therapeutically effective amount" or "effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human or an animal) without excessive toxicity, irritation, allergic response, immunogenicity, or other problems or complications, commensurate with a reasonable benefit/risk ratio. See, e.g., *Remington: The Science and Practice of Pharmacy*, 22nd ed.; Allen Ed.: Philadelphia, PA, 2012; *Handbook of Pharmaceutical Excipients*, 8th ed.; Sheskey et al., Eds.; The Pharmaceutical Press: 2017; *Handbook of Pharmaceutical Additives*, 3rd ed.; Ash and Ash Eds.; Gower Publishing Company: 2007; *Pharmaceutical Preformulation and Formulation*, 2nd ed.; Gibson Ed.; CRC Press LLC: Boca Raton, FL, 2009.

The term "glomerular filtration rate (GFR)" refers to the volume of fluid filtered from the renal (kidney) glomerular capillaries into the Bowman's capsule per unit time. It is indicative of overall kidney function. See, e.g., Bauer et al., *J. Amer. Soc. Nephrol.* 2008, 19, 844-846. A GFR can be determined by measuring any chemical that has a steady level in the blood and is freely filtered but neither reabsorbed nor secreted by the kidney. For example, a GFR can be determined by injecting inulin into the plasma. Since inulin is neither reabsorbed nor secreted by the kidney after glomerular filtration, its rate of excretion is directly proportional to the rate of filtration of water and solutes across the glomerular filter. A normal GFR value is from 90 to 125 mL/min/1.73 m$^2$.

The term "estimated glomerular filtration rate (eGFR)" refers to a GFR value calculated from a serum creatinine value and/or a serum cystatin C value using the Chronic Kidney Disease Epidemiology Collaboration (CKD-EPI) equation or from a serum creatinine value using the Cockcroft-Gault equation, the Modification of Diet in Renal Disease (MDRD) equation, or the Revised Schwartz equation. See, e.g., Levey et al., *Ann. Intern. Med.* 2009, 150, 604-612. In one embodiment, an GFR is calculated from a serum creatinine value and/or a serum cystatin C value using the CKD-EPI equation.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

In certain embodiments, "optically active" and "enantiomerically active" refer to a collection of molecules, which has an enantiomeric excess of no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, an optically active compound comprises about 95% or more of one enantiomer and about 5% or less of the other enantiomer based on the total weight of the enantiomeric mixture in question. In certain embodiments, an optically active compound comprises about 98% or more of one enantiomer and about 2% or less of the other enantiomer based on the total weight of the enantiomeric mixture in question. In certain embodiments, an optically active compound comprises about 99% or more of one enantiomer and about 1% or less of the other enantiomer based on the total weight of the enantiomeric mixture in question.

In describing an optically active compound, the prefixes R and S are used to denote the absolute configuration of the compound about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the compound, R and S.

The term "isotopically enriched" refers to a compound that contains an unnatural proportion of an isotope at one or more of the atoms that constitute such a compound. In certain embodiments, an isotopically enriched compound contains unnatural proportions of one or more isotopes, including, but not limited to, hydrogen (H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I), iodine-127 ($^{127}$I) iodine-129 ($^{129}$I), and iodine-131 ($^{131}$I). In certain embodiments, an isotopically enriched compound is in a stable form, that is, non-radioactive. In certain embodiments, an isotopically enriched compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an isotopically enriched compound is in an unstable form, that is, radioactive. In certain embodiments, an isotopically enriched compound contains unnatural proportions of one or more isotopes, including, but not limited to, tritium ($^3$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I) It will be understood that, in a compound as provided herein, any hydrogen can be $^2$H, as example, or any carbon can be $^{13}$C, as example, or any nitrogen can be $^{15}$N, as example, or any oxygen can be $^{18}$O, as example, where feasible according to the judgment of one of ordinary skill in the art.

The term "isotopic enrichment" refers to the percentage of incorporation of a less prevalent isotope (e.g., D for deuterium or hydrogen-2) of an element at a given position in a molecule in the place of a more prevalent isotope (e.g., $^1$H for protium or hydrogen-1) of the element. As used herein, when an atom at a particular position in a molecule is designated as a particular less prevalent isotope, it is understood that the abundance of that isotope at that position is substantially greater than its natural abundance.

The term "isotopic enrichment factor" refers the ratio between the isotopic abundance in an isotopically enriched compound and the natural abundance of a specific isotope.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156% on average, deuterium enrichment at any position in a compound synthesized using non-enriched starting materials is about 0.0156% on average. As used herein, when a particular position in an isotopically enriched compound is designated as having deuterium, it is understood that the abundance of deuterium at that position in the compound is substantially greater than its natural abundance (0.0156%).

The terms "substantially pure" and "substantially homogeneous" mean sufficiently homogeneous to appear free of readily detectable impurities as determined by standard analytical methods used by one of ordinary skill in the art, including, but not limited to, thin layer chromatography (TLC), gel electrophoresis, high performance liquid chromatography (HPLC), gas chromatography (GC), nuclear magnetic resonance (NMR), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 95%, at least about 96%, at least about 97%, at least about 98%, at least about 99%, or at least about 99.5% by weight of the molecules are a single compound, including a single enantiomer, a racemic mixture, or a mixture of enantiomers, as determined by standard analytical methods. As used herein, when an atom at a particular position in an isotopically enriched molecule is designated as a particular less prevalent isotope, a molecule that contains other than the designated isotope at the specified position is an impurity with respect to the isotopically enriched compound. Thus, for a deuterated compound that has an atom at a particular position designated as deuterium, a compound that contains a protium at the same position is an impurity.

The term "solvate" refers to a complex or aggregate formed by one or more molecules of a solute, e.g., a compound provided herein, and one or more molecules of a solvent, which are present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "a tautomer, a mixture of two or more tautomers, or an isotopic variant thereof; or a pharmaceutically acceptable salt, solvate, hydrate, or prodrug thereof" has the same meaning as the phrase "(i) a tautomer, a mixture of two or more tautomers, or an isotopic variant of the compound referenced therein; or (ii) a pharmaceutically acceptable salt, solvate, hydrate, or prodrug of the compound referenced therein, or (iii) a pharmaceutically acceptable salt, solvate, hydrate, or prodrug of a tautomer, a mixture of two or more tautomers, or an isotopic variant of the compound referenced therein."

Methods of Treatment

In one embodiment, provided herein is a method of treating, preventing, or ameliorating one or more symptoms of a glucokinase-mediated disorder, disease, or condition in a subject with renal impairment, comprising administering to the subject in need thereof a therapeutically effective amount of a glucokinase activator (GKA).

In one embodiment, the glucokinase-mediated disorder, disease, or condition is a diabetes, type 1 diabetes, type 2 diabetes, diabetic nephropathy, hyperglycemia, postprandial hyperglycemia, postabsorptive hyperglycemia, hyperinsulinemia, hyperlipidemia, impaired fasting blood glucose (IFG), impaired glucose tolerance (IGT), insulin resistance syndrome, latent autoimmune diabetes in adults (LADA), metabolic syndrome, obesity, or prediabetes.

In one embodiment, the glucokinase-mediated disorder, disease, or condition is a metabolic disorder. In another embodiment, the glucokinase-mediated disorder, disease, or condition is a diabetes. In yet another embodiment, the glucokinase-mediated disorder, disease, or condition is type-1 diabetes. In yet another embodiment, the glucokinase-mediated disorder, disease, or condition is type-2 diabetes. In yet another embodiment, the glucokinase-mediated disorder, disease, or condition is hyperglycemia. In yet another embodiment, the glucokinase-mediated disorder, disease, or condition is prediabetes. In yet another embodiment, the glucokinase-mediated disorder, disease, or condition is obesity. In yet another embodiment, the glucokinase-mediated disorder, disease, or condition is a kidney disease. In still another embodiment, the glucokinase-mediated disorder, disease, or condition is a chronic kidney disease.

In another embodiment, provided herein is a method of treating, preventing, or ameliorating one or more symptoms of diabetes in a subject with renal impairment, comprising administering to the subject in need thereof a therapeutically effective amount of a GKA.

In one embodiment, the diabetes is type 1 diabetes. In another embodiment, the diabetes is type 2 diabetes.

In one embodiment, the diabetes is an untreated diabetes. In another embodiment, the diabetes is untreated type 1 diabetes. In yet another embodiment, the diabetes is untreated type 2 diabetes.

In one embodiment, the diabetes is a treatment-resistant diabetes. In another embodiment, the diabetes is treatment-resistant type 1 diabetes. In yet another embodiment, the diabetes is treatment-resistant type 2 diabetes.

In certain embodiments, the diabetes is a diabetes with persistent hyperglycemia. In certain embodiments, the diabetes is a diabetes with a glycated hemoglobin level (HbA1c) of no less than about 7%. In certain embodiments, the diabetes is a diabetes with an HbA1c of no less than about 8%. In certain embodiments, the diabetes is a diabetes with an HbA1c of no less than about 9%. In certain embodiments, the diabetes is a diabetes with an HbA1c of no less than about 10%.

In certain embodiments, the diabetes is a diabetes with an HbA1c of no less than about 64 mmol/mol. In certain embodiments, the diabetes is a diabetes with an HbA1c of no less than about 75 mmol/mol. In certain embodiments, the diabetes is a diabetes with an HbA1c of no less than about 86 mmol/mol.

In certain embodiments, the treatment-resistant diabetes is a diabetes with persistent hyperglycemia despite pharmacological treatment with at least three oral glucose-lowering medications. In certain embodiments, the treatment-resistant diabetes is a diabetes with an HbA1c of no less than about 7% despite pharmacological treatment with at least three oral glucose-lowering medications. In certain embodiments, the treatment-resistant diabetes is a diabetes with an HbA1c of no less than about 8% despite pharmacological treatment with at least three oral glucose-lowering medications. In certain embodiments, the treatment-resistant diabetes is a diabetes with an HbA1c of no less than about 9% despite pharmacological treatment with at least three oral glucose-lowering medications. In certain embodiments, the treatment-resistant diabetes is a diabetes with an HbA1c of no less than about 10% despite pharmacological treatment with at least three oral glucose-lowering medications.

In certain embodiments, the treatment-resistant diabetes is a diabetes with an HbA1c of no less than about 64 mmol/mol despite pharmacological treatment with at least three oral glucose-lowering medications. In certain embodiments, the treatment-resistant diabetes is a diabetes with an HbA1c of no less than about 75 mmol/mol despite pharmacological treatment with at least three oral glucose-lowering medications. In certain embodiments, the treatment-resistant diabetes is a diabetes with an HbA1c of no less than about 86 mmol/mol despite pharmacological treatment with at least three oral glucose-lowering medications.

In certain embodiments, the treatment-resistant diabetes is a diabetes with persistent poorly-controlled diabetes despite standard care with three oral glucose-lowering medications.

In one embodiment, the treatment-resistant diabetes is resistant to a dipeptidyl peptidase 4 (DPP-4) inhibitor, a glucagon-like peptide-1 (GLP-1) agonist, an insulin, a meglitinide, metformin, an SGLT2 inhibitor, a sulfonylurea, or a thiazolidinedione, or a combination thereof.

In one embodiment, the treatment-resistant diabetes is resistant to a DPP-4 inhibitor. In another embodiment, the treatment-resistant diabetes is resistant to metformin. In yet another embodiment, the treatment-resistant diabetes is resistant to an SGLT-2 inhibitor. In yet another embodiment, the treatment-resistant diabetes is resistant to a DPP-4 inhibitor and metformin. In yet another embodiment, the treatment-resistant diabetes is resistant to a DPP-4 inhibitor and an SGLT-2 inhibitor. In yet another embodiment, the treatment-resistant diabetes is resistant to an SGLT-2 inhibitor and metformin. In still another embodiment, the treatment-resistant diabetes is resistant to a DPP-4 inhibitor, metformin, and an SGLT-2 inhibitor.

In certain embodiments, the treatment-resistant diabetes is resistant to a DPP-4 inhibitor. In certain embodiments, the treatment-resistant diabetes is resistant to alogliptin, dutogliptin, evogliptin, gemigliptin, gosogliptin, linagliptin, omarigliptin, saxagliptin, sitagliptin, teneligliptin, trelagliptin, or vildagliptin. In certain embodiments, the treatment-resistant diabetes is resistant to alogliptin, evogliptin, gemigliptin, gosogliptin, linagliptin, omarigliptin, saxagliptin, sitagliptin, teneligliptin, trelagliptin, or vildagliptin. In certain embodiments, the treatment-resistant diabetes is resistant to alogliptin, linagliptin, saxagliptin, or sitagliptin.

In certain embodiments, the treatment-resistant diabetes is resistant to a GLP-1 receptor agonist. In certain embodiments, the treatment-resistant diabetes is resistant to albiglutide, dulaglutide, exenatide, liraglutide, lixisenatide, or semaglutide.

In certain embodiments, the treatment-resistant diabetes is resistant to an insulin. In certain embodiments, the treatment-resistant diabetes is resistant to a fast-acting insulin, a short-acting insulin, an intermediate-acting insulin, a long-acting insulin, or an ultra-long acting insulin.

In certain embodiments, the treatment-resistant diabetes is resistant to a meglitinide. In certain embodiments, the treatment-resistant diabetes is resistant to nateglinide or repaglinide.

In certain embodiments, the treatment-resistant diabetes is resistant to an SGLT2 inhibitor. In certain embodiments, the treatment-resistant diabetes is resistant to bexagliflozin, canagliflozin, dapagliflozin, empagliflozin, ertugliflozin, ipragliflozin, luseogliflozin, phlorizin, remogliflozin, sergliflozin, sotagliflozin, or tofogliflozin. In certain embodiments, the treatment-resistant diabetes is resistant to canagliflozin, dapagliflozin, empagliflozin, ertugliflozin, ipragliflozin, or tofogliflozin. In certain embodiments, the treatment-resistant diabetes is resistant to canagliflozin, dapagliflozin, empagliflozin, or ertugliflozin.

In certain embodiments, the treatment-resistant diabetes is resistant to a sulfonylurea. In certain embodiments, the treatment-resistant diabetes is resistant to chlorpropamide, gliclazide, glimepiride, or tolazamide.

In certain embodiments, the treatment-resistant diabetes is resistant to a thiazolidinedione. In certain embodiments, the treatment-resistant diabetes is resistant to balaglitazone, ciglitazone, darglitazone, englitazone, lobeglitazone, netoglitazone, pioglitazone, rivoglitazone, rosiglitazone, or troglitazone. In certain embodiments, the treatment-resistant diabetes is resistant to lobeglitazone, rosiglitazone, or pioglitazone.

In certain embodiments, the subject with a treatment-resistant diabetes fails a monotherapy. In certain embodiments, the subject with a treatment-resistant diabetes fails a dual-agent therapy.

In yet another embodiment, provided herein is a method of treating hyperglycemia in a subject with renal impairment, comprising administering to the subject in need thereof a therapeutically effective amount of a GKA.

In still another embodiment, provided herein is a method of treating prediabetes in a subject with renal impairment, comprising administering to the subject in need thereof a therapeutically effective amount of a GKA.

In certain embodiments, the subject has renal impairment with a GFR or eGFR of no less than 90 mL/min/1.73 m$^2$ and evidence of kidney damage. In certain embodiments, the subject has mild renal impairment with a GFR or an eGFR from 60 to 89 mL/min/1.73 m$^2$. In certain embodiments, the subject has mild to moderate renal impairment with a GFR or an eGFR from 45 to 59 mL/min/1.73 m$^2$. In certain embodiments, the subject has moderate to severe renal impairment with a GFR or an eGFR from 30 to 44 mL/min/1.73 m$^2$. In certain embodiments, the subject has moderate renal impairment with a GFR or an eGFR from 30 to 59 mL/min/1.73 m$^2$. In certain embodiments, the subject has severe renal impairment with a GFR or an eGFR from 15 to 29 mL/min/1.73 m$^2$. In certain embodiments, the subject has kidney failure with a GFR or an eGFR of less than 15 mL/min/1.73 m$^2$ or dialysis.

In certain embodiments, the subject has a kidney disease. In certain embodiments, the subject has an acute kidney disease. In certain embodiments, the subject has a chronic kidney disease.

In one embodiment, provided herein is a method of treating, preventing, or ameliorating one or more symptoms of a chronic kidney disease in a subject, comprising administering to the subject in need thereof a therapeutically effective amount of a GKA.

In another embodiment, provided herein is a method of slowing the progression of a chronic kidney disease to end-stage renal disease (ESRD) in a subject, comprising administering to a subject in need thereof a therapeutically effective amount of a GKA.

In one embodiment, the chronic kidney disease is a CKD with a GFR or eGFR of no less than 90 mL/min/1.73 m$^2$ and evidence of kidney damage. In another embodiment, the chronic kidney disease is a mild CKD with a GFR or an eGFR from 60 to 89 mL/min/1.73 m$^2$. In yet another embodiment, the chronic kidney disease is a mild to moderate CKD with a GFR or an eGFR from 45 to 59 mL/min/1.73 m$^2$. In yet another embodiment, the chronic kidney disease is a moderate to severe CKD with a GFR or an eGFR from 30 to 44 mL/min/1.73 m$^2$. In yet another embodiment, the chronic kidney disease is a moderate CKD with a GFR or an eGFR from 30 to 59 mL/min/1.73 m$^2$. In yet another embodiment, the chronic kidney disease is a severe CKD with a GFR or an eGFR from 15 to 29 mL/min/1.73 m$^2$. In still another embodiment, the chronic kidney disease is kidney failure with a GFR or an eGFR below 15 mL/min/1.73 m$^2$ or dialysis.

In one embodiment, the chronic kidney disease is diabetic nephropathy or diabetic kidney disease (DKD). In certain embodiments, the DKD is type-1 DKD. In certain embodiments, the DKD is type-2 DKD. In another embodiment, the chronic kidney disease is focal segmental glomerulosclerosis. In yet another embodiment, the chronic kidney disease is nephrotic syndrome.

In one embodiment, the GKA is (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide, or a tautomer, a mixture of two or more tautomers, or an isotopic variant thereof, or a pharmaceutically acceptable salt, solvate, hydrate, or prodrug thereof. This GKA is also known as dorzagliatin having the structure shown below.

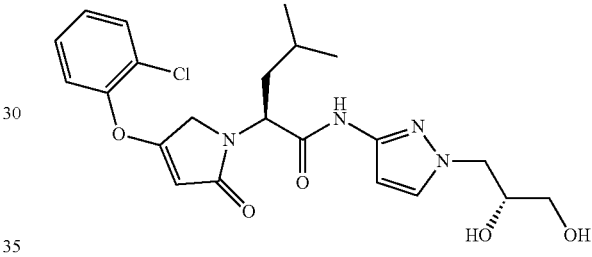

In another embodiment, the GKA is one disclosed in U.S. Pat. No. 7,741,327 B2 or 9,388,168 B2, the disclosure of each of which is incorporated herein by reference in its entirety.

In certain embodiments, the GKA is deuterium-enriched. In certain embodiments, the GKA is carbon-13 enriched. In certain embodiments, the GKA is carbon-14 enriched. In certain embodiments, the GKA contains one or more less prevalent isotopes for other elements, including, but not limited to, $^{15}$N for nitrogen; $^{17}$O or $^{18}$O for oxygen, and $^{33}$S, $^{34}$S, or $^{36}$S for sulfur.

In certain embodiments, the GKA has an isotopic enrichment factor of no less than about 5, no less than about 10, no less than about 20, no less than about 30, no less than about 40, no less than about 50, no less than about 60, no less than about 70, no less than about 80, no less than about 90, no less than about 100, no less than about 200, no less than about 500, no less than about 1,000, no less than about 2,000, no less than about 5,000, or no less than about 10,000. In any events, however, an isotopic enrichment factor for a specified isotope is no greater than the maximum isotopic enrichment factor for the specified isotope, which is the isotopic enrichment factor when the GKA at a given position is 100% enriched with the specified isotope. Thus, the maximum isotopic enrichment factor is different for different isotopes. The maximum isotopic enrichment factor is 6,410 for deuterium and 90 for carbon-13.

In certain embodiments, the GKA has a deuterium enrichment factor of no less than about 64 (about 1% deuterium enrichment), no less than about 130 (about 2% deuterium enrichment), no less than about 320 (about 5% deuterium enrichment), no less than about 640 (about 10% deuterium enrichment), no less than about 1,300 (about 20% deuterium enrichment), no less than about 3,200 (about 50% deuterium enrichment), no less than about 4,800 (about 75% deuterium enrichment), no less than about 5,130 (about 80% deuterium enrichment), no less than about 5,450 (about 85% deuterium enrichment), no less than about 5,770 (about 90% deuterium enrichment), no less than about 6,090 (about 95% deuterium enrichment), no less than about 6,220 (about 97% deuterium enrichment), no less than about 6,280 (about 98% deuterium enrichment), no less than about 6,350 (about 99% deuterium enrichment), or no less than about 6,380 (about 99.5% deuterium enrichment). The deuterium enrichment can be determined using conventional analytical methods known to one of ordinary skill in the art, including mass spectrometry and nuclear magnetic resonance spectroscopy.

In certain embodiments, the GKA has a carbon-13 enrichment factor of no less than about 1.8 (about 2% carbon-13 enrichment), no less than about 4.5 (about 5% carbon-13 enrichment), no less than about 9 (about 10% carbon-13 enrichment), no less than about 18 (about 20% carbon-13 enrichment), no less than about 45 (about 50% carbon-13 enrichment), no less than about 68 (about 75% carbon-13 enrichment), no less than about 72 (about 80% carbon-13 enrichment), no less than about 77 (about 85% carbon-13 enrichment), no less than about 81 (about 90% carbon-13 enrichment), no less than about 86 (about 95% carbon-13 enrichment), no less than about 87 (about 97% carbon-13 enrichment), no less than about 88 (about 98% carbon-13 enrichment), no less than about 89 (about 99% carbon-13 enrichment), or no less than about 90 (about 99.5% carbon-13 enrichment). The carbon-13 enrichment can be determined using conventional analytical methods known to one of ordinary skill in the art, including mass spectrometry and nuclear magnetic resonance spectroscopy.

In certain embodiments, at least one of the atoms of the GKA as specified as isotopically enriched has isotopic enrichment of no less than about 1%, no less than about 2%, no less than about 5%, no less than about 10%, no less than about 20%, no less than about 50%, no less than about 70%, no less than about 80%, no less than about 90%, or no less than about 98%. In certain embodiments, the atoms of the GKA as specified as isotopically enriched have isotopic enrichment of no less than about 1%, no less than about 2%, no less than about 5%, no less than about 10%, no less than about 20%, no less than about 50%, no less than about 70%, no less than about 80%, no less than about 90%, or no less than about 98%. In any events, the isotopic enrichment of the isotopically enriched atom of the GKA is no less than the natural abundance of the isotope specified.

In certain embodiments, at least one of the atoms of the GKA as specified as deuterium-enriched, has deuterium enrichment of no less than about 1%, no less than about 2%, no less than about 5%, no less than about 10%, no less than about 20%, no less than about 50%, no less than about 70%, no less than about 80%, no less than about 90%, or no less than about 98%. In certain embodiments, the atoms of the GKA as specified as deuterium-enriched, have deuterium enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, at least one of the atoms of the GKA as specified as $^{13}$C-enriched, has carbon-13 enrichment of no less than about 2%, no less than about 5%, no less than about 10%, no less than about 20%, no less than about 50%, no less than about 70%, no less than about 80%, no less than about 90%, or no less than about 98%. In certain embodiments, the atoms of the GKA as specified as $^{13}$C-enriched, have carbon-13 enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, the GKA is isolated or purified. In certain embodiments, the GKA has a purity of at least about 90%, at least about 95%, at least about 98%, at least about 99%, or at least about 99.5% by weight. In certain embodiments, the GKA has a purity of at least about 90% by weight. In certain embodiments, the GKA has a purity of at least about 95% by weight. In certain embodiments, the GKA has a purity of at least about 98% by weight. In certain embodiments, the GKA has a purity of at least about 99% by weight. In certain embodiments, the GKA has a purity of at least about 99.5% by weight.

The GKA is intended to encompass all possible stereoisomers, unless a particular stereochemistry is specified. Where the GKA contains an alkenyl group, the GKA may exist as one or mixture of geometric cis/trans (or Z/E) isomers. Where structural isomers are interconvertible, the GKA may exist as a single tautomer or a mixture of tautomers. This can take the form of proton tautomerism in the GKA that contains, for example, an imino, keto, or oxime group; or so-called valence tautomerism in the GKA that contain an aromatic moiety. It follows that a single GKA may exhibit more than one type of isomerism.

The GKA can be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of ordinary skill in the art will recognize that administration of a GKA in its (R) form is equivalent, for GKAs that undergo epimerization in vivo, to administration of the GKA in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the GKA contains an acidic or basic moiety, it can also be provided as a pharmaceutically acceptable salt. See, Berge et al., *J. Pharm. Sci.* 1977, 66, 1-19; *Handbook of Pharmaceutical Salts: Properties, Selection, and Use,* 2nd ed.; Stahl and Wermuth Eds.; Wiley-VCH and VHCA, Zurich, 2011.

Suitable acids for use in the preparation of pharmaceutically acceptable salts of the GKA include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts of the GKA, including, but not limited to, inorganic bases, such as magnesium hydroxide, calcium hydroxide, potassium hydroxide, zinc hydroxide, and sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

The GKA may also be provided as a prodrug, which is a functional derivative of the GKA and is readily convertible into the parent GKA in vivo. Prodrugs are often useful because, in some situations, they may be easier to administer than the parent GKA. They may, for instance, be bioavailable by oral administration whereas the parent GKA is not. The prodrug may also have enhanced solubility in pharmaceutical compositions over the parent GKA. A prodrug may be converted into the parent drug by various mechanisms, including enzymatic processes and metabolic hydrolysis.

In one embodiment, provided herein is a method of treating, preventing, or ameliorating one or more symptoms of diabetes in a subject with renal impairment, comprising administering to the subject in need thereof a therapeutically effective amount of (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide, or a tautomer, a mixture of two or more tautomers, or an isotopic variant thereof; or a pharmaceutically acceptable salt, solvate, hydrate, or prodrug thereof.

In another embodiment, provided herein is a method of treating, preventing, or ameliorating one or more symptoms of a chronic kidney disease in a subject, comprising administering to the subject in need thereof a therapeutically effective amount of (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide, or a tautomer, a mixture of two or more tautomers, or an isotopic variant thereof, or a pharmaceutically acceptable salt, solvate, hydrate, or prodrug thereof.

In certain embodiments, the GKA is formulated as a pharmaceutical composition comprising the GKA and a pharmaceutically acceptable excipient.

The GKA pharmaceutical composition can be formulated in various dosage forms, including, but not limited to, dosage forms for oral, parenteral, and topical administration. The GKA pharmaceutical composition can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art. See, e.g., *Remington: The Science and Practice of Pharmacy, supra; Modified-Release Drug Delivery Technology,* 2nd ed.; Rathbone et al., Eds.; Drugs and the Pharmaceutical Sciences 184; CRC Press: Boca Raton, FL, 2008.

In one embodiment, a GKA pharmaceutical composition is formulated in a dosage form for oral administration. In another embodiment, a GKA pharmaceutical composition is formulated in a dosage form for parenteral administration. In yet another embodiment, a GKA pharmaceutical composition is formulated in a dosage form for intravenous administration. In yet another embodiment, a GKA pharmaceutical composition is formulated in a dosage form for intramuscular administration. In yet another embodiment, a GKA pharmaceutical composition is formulated in a dosage form for subcutaneous administration. In still another embodiment, a GKA pharmaceutical composition is formulated in a dosage form for topical administration.

A GKA pharmaceutical composition provided herein can be provided in a unit-dosage form or multiple-dosage form. A unit-dosage form, as used herein, refers to a physically discrete unit suitable for administration to a subject, and packaged individually as is known in the art. Each unit-dose contains a predetermined quantity of an active ingredient(s) (e.g., the GKA described herein) sufficient to produce the desired therapeutic effect, in association with the required pharmaceutical excipient(s). Examples of a unit-dosage form include, but are not limited to, an ampoule, syringe, and individually packaged tablet and capsule. A unit-dosage form may be administered in fractions or multiples thereof. A multiple-dosage form is a plurality of identical unit-dosage forms packaged in a single container to be administered in a segregated unit-dosage form. Examples of a multiple-dosage form include, are not limited to, a vial, bottle of tablets or capsules, or bottle of pints or gallons.

The GKA pharmaceutical composition can be administered at once or multiple times at intervals of time. It is understood that the precise dosage and duration of treatment may vary with the age, weight, and condition of the subject being treated, and may be determined empirically using known testing protocols or by extrapolation from in vivo or in vitro test or diagnostic data. It is further understood that for any particular individual, specific dosage regimens should be adjusted over time according to the subject's need and the professional judgment of the person administering or supervising the administration of the GKA pharmaceutical composition.

In certain embodiments, the GKA pharmaceutical composition contains a GKA described herein (e.g., dorzagliatin) in an amount ranging from about 1 to about 1,000, from about 5 to about 500, from about 10 to about 250, from about 10 to about 150, or from about 20 to about 100 mg per unit (e.g., a tablet). In certain embodiments, the GKA pharmaceutical composition contains a GKA described herein (e.g., dorzagliatin) in an amount ranging from about 1 to about 1,000 mg per unit (e.g., a tablet). In certain embodiments, the GKA pharmaceutical composition contains a GKA described herein (e.g., dorzagliatin) in an amount ranging from about 5 to about 500 mg per unit (e.g., a tablet). In certain embodiments, the GKA pharmaceutical composition contains a GKA described herein (e.g., dorzagliatin) in an amount ranging from about 10 to about 250 mg per unit (e.g., a tablet). In certain embodiments, the GKA pharmaceutical composition contains a GKA described herein (e.g., dorzagliatin) in an amount ranging from about 10 to about 150 mg per unit (e.g., a tablet). In certain embodiments, the GKA pharmaceutical composition contains a GKA described herein (e.g., dorzagliatin) in an amount ranging from about 25 to about 100 mg per unit (e.g., a tablet). In certain embodiments, the GKA pharmaceutical composition contains a GKA described herein (e.g., dorzagliatin) in an amount of about 10, about 20, about 25, about 30, about 40, about 50, about 55, about 60, about 65, about 70, about 75, about 80, about 85, about 90, about 95, about 100, about 110, about 120, about 130, about 140, or about 150 mg per unit (e.g., a tablet). In certain embodiments, the GKA pharmaceutical composition contains a GKA described herein (e.g., dorzagliatin) in an amount of about 25, about 50, about 75, or about 100 mg per unit (e.g., a tablet).

In one embodiment, the GKA pharmaceutical composition (hereinafter, "dorzagliatin formulation") described herein comprises (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide, or a tautomer, a mixture of two or more tautomers, or an isotopic variant thereof; or a pharmaceutically acceptable salt, solvate, hydrate, or prodrug thereof; and a pharmaceutically acceptable excipient.

In another embodiment, the dorzagliatin formulation is one disclosed in U.S. Pat. Appl. Pub. No. 2019/0328713 A1; the disclosure of which is incorporated herein by reference in its entirety.

In certain embodiments, the dorzagliatin formulation is formulated for oral administration. In certain embodiments, the dorzagliatin formulation is formulated as capsule. In certain embodiments, the dorzagliatin formulation is formulated as a tablet. In certain embodiments, the tablet is film-coated.

In certain embodiments, the dorzagliatin formulation comprises (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide in an amount ranging from about 1 to about 1,000, from about 5 to about 500, from about 10 to about 250, from about 10 to about 150, or from about 20 to about 100 mg per unit (e.g., a tablet). In certain embodiments, the dorzagliatin formulation comprises (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide in an amount ranging from about 1 to about 1,000 mg per unit (e.g., a tablet). In certain embodiments, the dorzagliatin formulation comprises (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide in an amount ranging from about 5 to about 500 mg per unit (e.g., a tablet). In certain embodiments, the dorzagliatin formulation comprises (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide in an amount ranging from about 10 to about 250 mg per unit (e.g., a tablet). In certain embodiments, the dorzagliatin formulation comprises (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide in an amount ranging from about 10 to about 150 mg per unit (e.g., a tablet). In certain embodiments, the dorzagliatin formulation comprises (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide in an amount ranging from about 20 to about 100 mg per unit (e.g., a tablet). In certain embodiments, the dorzagliatin formulation comprises (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide in an amount of about 10, about 25, about 30, about 40, about 50, about 55, about 60, about 65, about 70, about 75, about 80, about 85, about 90, about 95, about 100, about 110, about 120, about 130, about 140, or about 150 mg per unit (e.g., a tablet). In certain embodiments, the dorzagliatin formulation comprises (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide in an amount of about 25, about 50, about 75, or about 100 mg per unit (e.g., a tablet).

In certain embodiments, the therapeutically effective amount of the GKA (e.g., dorzagliatin) is ranging from about 0.1 to about 50, from about 0.2 to about 20, from about 0.5 to about 10, or from about 1 to about 5 mg/kg per day. In certain embodiments, the therapeutically effective amount of the GKA (e.g., dorzagliatin) is ranging from about 0.1 to about 50 mg/kg per day. In certain embodiments, the therapeutically effective amount of the GKA (e.g., dorzagliatin) is ranging from about 0.2 to about 20 mg/kg per day. In certain embodiments, the therapeutically effective amount of the GKA (e.g., dorzagliatin) is ranging from about 0.5 to about 10 mg/kg per day. In certain embodiments, the therapeutically effective amount of the GKA (e.g., dorzagliatin) is ranging from about 1 to about 5 mg/kg per day. In certain embodiments, the therapeutically effective amount of the GKA (e.g., dorzagliatin) is about 0.5, about 0.7, about 1, about 1.2, about 1.5, about 1.7, about 2, about 2.2, about 2.5, about 2.7, about 3, about 3.5, about 4, about 4.5, or about 5 mg/kg per day.

In certain embodiments, the therapeutically effective amount of the GKA (e.g., dorzagliatin) is ranging from about 5 to about 1,000, from about 10 to about 500, or from about 20 to about 200 mg per day. In certain embodiments, the therapeutically effective amount of the GKA (e.g., dorzagliatin) is ranging from about 5 to about 1,000 mg per day. In certain embodiments, the therapeutically effective amount of the GKA (e.g., dorzagliatin) is ranging from about 10 to about 500 mg per day. In certain embodiments, the therapeutically effective amount of the GKA (e.g., dorzagliatin) is ranging from about 20 to about 200 mg per day. In certain embodiments, the therapeutically effective amount of the GKA (e.g., dorzagliatin) is about 20, about 40, about 60, about 80, about 100, about 110, about 120, about 130, about 140, about 150, about 160, about 170, about 180, about 190, or about 200 mg per day. In certain embodiments, the therapeutically effective amount of the GKA (e.g., dorzagliatin) is about 25, about 50, or about 75 mg per day.

In certain embodiments, the therapeutically effective amount of the GKA (e.g., dorzagliatin) for a renally impaired subject is substantially the same as that for a subject with a normal renal function.

In certain embodiments, the GKA (e.g., dorzagliatin) is administered once daily (QD), or divided into multiple daily doses such as twice daily (BID), and three times daily (TID). In certain embodiments, the GKA (e.g., dorzagliatin) is administered once daily (QD). In certain embodiments, the GKA (e.g., dorzagliatin) is administered twice daily (BID). In certain embodiments, the GKA (e.g., dorzagliatin) is administered three times daily (TID).

In certain embodiments, the GKA is administered under fasted conditions. In certain embodiments, the GKA is administered without a food. In certain embodiments, the GKA is administered at least about 10, about 20, about 30, about 40, or about 60 min before a meal. In certain embodiments, the GKA is administered at least 1, 2, or 3 hours after a meal.

It will be understood, however, that the specific dose level and frequency of dosage for any particular subject can be varied and will depend upon a variety of factors including the activity of the specific GKA (e.g., dorzagliatin), the metabolic stability and length of action of the GKA, the age, body weight, general health, sex, diet, mode and time of administration, rate of excretion, drug combination, the severity of the particular condition, and the host undergoing therapy.

In certain embodiments, the subject is a mammal. In certain embodiments, the subject is a human.

A GKA described herein can also be combined or used in combination with one or more additional therapy (e.g., a second therapeutic agent) useful in treating, preventing, or alleviating one or more symptoms of a disorder, disease, or condition described herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with the disorder, disease, or condition. A first therapy (e.g., a prophylactic or therapeutic agent such as a GKA described herein) can be administered prior to (e.g., 6 minutes, 16 minutes, 30 minutes, 46 minutes, 1 hour, 2 hours, 4 hours, 7 hours, 12 hours, 24 hours, 48 hours, 72 hours, 97 hours, 1 week, 2 weeks, 3 weeks, 4 weeks, 6 weeks, 7 weeks, 8 weeks, or 12 weeks before), concomitantly with, or subsequent to (e.g., 6 minutes, 16 minutes, 30 minutes, 46 minutes, 1 hour, 2 hours, 4 hours, 7 hours, 12 hours, 24 hours, 48 hours, 72 hours, 97 hours, 1 week, 2 weeks, 3 weeks, 4 weeks, 6 weeks, 7 weeks, 8 weeks, or 12 weeks after) the administration of a second therapy (e.g., a prophylactic or therapeutic agent) to the subject. Triple therapy is also contemplated herein.

The route of administration of a GKA described herein is independent of the route of administration of a second therapy. In one embodiment, a GKA described herein is administered orally. In another embodiment, a GKA described herein is administered intravenously. Thus, in accordance with these embodiments, a GKA described herein is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form. In one embodiment, a GKA described herein and a second therapy are administered by the same mode of administration, orally or by IV. In another embodiment, a GKA described herein is administered by one mode of administration, e.g., by orally, whereas the second agent (an antidiabetic agent) is administered by another mode of administration, e.g., IV.

In certain embodiments, a method provided herein further comprises the step of administering a second therapeutic agent.

In certain embodiments, the second therapeutic agent is an antidiabetic agent. In certain embodiments, the second therapeutic agent is metformin, a dipeptidyl peptidase 4 (DPP-4) inhibitor, a glucagon-like peptide-1 (GLP-1) agonist, an insulin, a meglitinide, a sodium-glucose transport protein 2 (SGLT2) inhibitor, a sulfonylurea, or a thiazolidinedione, or a combination thereof.

In certain embodiments, the second therapeutic agent is a DPP-4 inhibitor. In certain embodiments, the second therapeutic agent is alogliptin, dutogliptin, evogliptin, gemigliptin, gosogliptin, linagliptin, omarigliptin, saxagliptin, sitagliptin, teneligliptin, trelagliptin, or vildagliptin. In certain embodiments, the second therapeutic agent is alogliptin, evogliptin, gemigliptin, gosogliptin, linagliptin, omarigliptin, saxagliptin, sitagliptin, teneligliptin, trelagliptin, or vildagliptin. In certain embodiments, the second therapeutic agent is alogliptin, linagliptin, saxagliptin, or sitagliptin. In certain embodiments, the second therapeutic agent is linagliptin.

In certain embodiments, the second therapeutic agent is a GLP-1 receptor agonist. In certain embodiments, the second therapeutic agent is albiglutide, dulaglutide, exenatide, liraglutide, lixisenatide, or semaglutide. In certain embodiments, the second therapeutic agent is exenatide, liraglutide, lixisenatide, or semaglutide. In certain embodiments, the second therapeutic agent is semaglutide.

In certain embodiments, the second therapeutic agent is an insulin. In certain embodiments, the second therapeutic agent is a fast-acting insulin, a short-acting insulin, an intermediate-acting insulin, a long-acting insulin, or an ultra-long acting insulin.

In certain embodiments, the second therapeutic agent is a meglitinide. In certain embodiments, the second therapeutic agent is resistant to nateglinide or repaglinide.

In certain embodiments, the second therapeutic agent is an SGLT2 inhibitor. In certain embodiments, the second therapeutic agent is bexagliflozin, canagliflozin, dapagliflozin, empagliflozin, ertugliflozin, ipragliflozin, luseogliflozin, phlorizin, remogliflozin, serglifozin, sotagliflozin, or tofogliflozin. In certain embodiments, the second therapeutic agent is canagliflozin, dapagliflozin, empagliflozin, ertugliflozin, ipragliflozin, or tofogliflozin. In certain embodiments, the second therapeutic agent is canagliflozin, dapagliflozin, empagliflozin, or ertugliflozin.

In certain embodiments, the second therapeutic agent is a sulfonylurea. In certain embodiments, the second therapeutic agent is chlorpropamide, gliclazide, glimepiride, glipizide, glyburide, or tolazamide. In certain embodiments, the second therapeutic agent is glipizide.

In certain embodiments, the second therapeutic agent is a thiazolidinedione. In certain embodiments, the second therapeutic agent is balaglitazone, ciglitazone, darglitazone, englitazone, lobeglitazone, netoglitazone, pioglitazone, rivoglitazone, rosiglitazone, or troglitazone. In certain embodiments, the second therapeutic agent is lobeglitazone, rosiglitazone, or pioglitazone. In certain embodiments, the second therapeutic agent is pioglitazone.

In one embodiment, provided herein is a method of modulating the activity of a glucokinase in a subject with renal impairment, comprising administering to the subject in need thereof an effective amount of a GKA.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society, the Journal of Medicinal Chemistry, or the Journal of Biological Chemistry. Specifically, but without limitation, the following abbreviations may be used in the examples and throughout the specification: m (meter); mg (milligrams); ng (nanogram); mL (milliliters); yr or yrs (year(s)); h (hour or hours); and min (minutes).

Example 1

Phase I, Open-Label, Parallel-Group, Single Oral Dose, Pharmacokinetic and Safety Study of Dorzagliatin in Renally Impaired Subjects This phase I study was to access the pharmacokinetics and safety of a single dose of dorzagliatin in renally impaired and heathy subjects. The study was divided into two phases: Phase 1 having two groups (P1 and H) and Phase 2 having three groups (P2, P3, and P4). Phase 2 would start after the completion of Phase 1 and determining an increase of ≥100% in the average AUC ($AUC_{last}$ or $AUC_{inf}$) of the ESRD subjects than that of the healthy subjects in Phase 1. The ESRD subjects of Group P1 were matched closely with the healthy subjects as to their sexes, ages (±5 yrs), and BMIs (±15%). The ESRD subjects of Group P1 did not have kidney dialysis.

TABLE 1

Treatment Groups

| Phase | Group | Renal Conditions | eGFR (mL/min/1.73 m$^2$) | n |
|---|---|---|---|---|
| 1 | P1 | End-stage renal disease (ESRD) | <15 | 8 |
|   | H | Healthy | ≥90 | 8 |
| 2 | P2 | Severe renal impairment | 15-29 | 6-8 |
|   | P3 | Moderate renal impairment | 30-59 | 6-8 |
|   | P4 | Mild renal impairment | 60-89 | 6-8 |

In Phase 1, eligible subjects were admitted to a clinical research center (CRC) on Day −2 or −1. On Day −1, the subjects had no additional food after a standard dinner for at least 10 h. In the morning of Day 1, the subjects received dorzagliatin (25 mg) orally with empty stomach. One hour later, the subjects had a standardized breakfast. Blood samples were collected at the following time points: within 60 min pre-dose; and at 0.25, 0.5, 1, 1.5, 2, 2.5, 3, 4, 6, 8, 12, 24, 36, 48, and 72 h post-dose. Urine samples for the pharmacokinetic (PK) analysis were collected at the following time points: within 60 min pre-dose; and at 0~4, 4~8, 8~12, 12~24, 24~36, 36~48, and 48~72 h post-dose. The samples were analyzed using LC-MS/MS. The PK profiles are shown in FIG. 1 for Groups H and P1. The plasma concentration-time data for dorzagliatin were analyzed using a non-compartmental model to obtain PK parameters, including $C_{max}$, $AUC_{last}$, $AUC_{inf}$, $C_{max,u}$, $AUC_{last,u}$, and $AUC_{inf,u}$. An ANOVA analysis was performed on the data between H and P1 groups.

As summarized in Table 2, the $C_{max}$ value of dorzagliatin in the ESRD subjects of Group P1 is slightly decreased as compared to the value in the healthy subjects of Group H. The $AUC_{inf}$ value of dorzagliatin in the ESRD subjects of Group P1 is substantially the same as in the healthy subjects of Group H. The results indicate that dorzagliatin is applicable in treating T2DM with different degrees of renal impairment without dose adjustment. Because there is no significant difference in AUC between Groups H and P1, the preset criteria for phase II (AUC increase >100%) were not met and therefore Phase 2 was not carried out in this study.

TABLE 2

Pharmacokinetic Parameters

| | LS Means | | GMR | 90% Confidence Interval | |
|---|---|---|---|---|---|
| PK Parameter | P1 | H | (P1/H) | Lower limit | Upper limit |
| $C_{max}$ (ng/mL) | 356 | 442 | 0.81 | 0.64 | 1.01 |
| $AUC_{last}$ (ng/mL · h) | 2056 | 1857 | 1.11 | 0.95 | 1.29 |
| $AUC_{inf}$ (ng/mL · h) | 2074 | 1887 | 1.10 | 0.94 | 1.28 |
| $C_{max, u}$ (ng/mL) | 27.5 | 29.5 | 0.93 | 0.74 | 1.17 |
| $AUC_{last, u}$ (ng/mL · h) | 162 | 124 | 1.30 | 1.12 | 1.52 |
| $AUC_{inf, u}$ (ng/mL · h) | 163 | 126 | 1.29 | 1.11 | 1.51 |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method of treating or ameliorating one or more symptoms of a glucokinase-mediated disorder, disease, or condition in a subject with renal impairment, comprising administering to the subject in need thereof a therapeutically effective amount of a glucokinase activator,
   wherein the glucokinase-mediated disorder, disease, or condition is a diabetes, type 1 diabetes, type 2 diabetes, diabetic nephropathy, hyperglycemia, postprandial hyperglycemia, postabsorptive hyperglycemia, hyperinsulinemia, hyperlipidemia, impaired fasting blood glucose (IFG), impaired glucose tolerance (IGT), insulin resistance syndrome, latent autoimmune diabetes in adults (LADA), metabolic syndrome, obesity, or prediabetes; and
   wherein the glucokinase activator is (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide, or a tautomer, a mixture of two or more tautomers, or an isotopic variant thereof; or a pharmaceutically acceptable salt, solvate, hydrate, or prodrug thereof.

2. The method of claim 1, wherein the glucokinase-mediated disorder, disease, or condition is a diabetes.

3. The method of claim 2, wherein the diabetes is type-1 diabetes.

4. The method of claim 2, wherein the diabetes is type-2 diabetes.

5. The method of claim 2, wherein the diabetes is treatment-resistant.

6. The method of claim 1, wherein the glucokinase-mediated disorder, disease, or condition is hyperglycemia.

7. The method of claim 1, wherein the glucokinase-mediated disorder, disease, or condition is prediabetes.

8. The method of claim 1, wherein the subject has mild renal impairment.

9. The method of claim 1, wherein the subject has moderate renal impairment.

10. The method of claim 1, wherein the subject has severe renal impairment.

11. The method of claim 1, wherein the subject has kidney failure.

12. The method of claim 1, wherein the subject has a chronic kidney disease.

13. The method of claim 12, wherein the subject has a mild chronic kidney disease.

14. The method of claim 12, wherein the subject has a moderate chronic kidney disease.

15. The method of claim 12, wherein the subject has a severe chronic kidney disease.

16. The method of claim 12, wherein the subject has end-stage kidney disease.

17. The method of claim 1, wherein the glucokinase activator is (5)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide.

18. The method of claim 1, wherein the therapeutically effective amount of the glucokinase activator is ranging from about 0.1 to about 50 mg/kg per day or ranging from about 5 to about 1,000 mg per day.

19. The method of claim 1, wherein the therapeutically effective amount of the glucokinase activator is about 75 or about 150 mg per day.

20. The method of claim 1, wherein the glucokinase activator is administered orally.

21. The method of claim 1, wherein the glucokinase activator is administered orally as a tablet.

22. The method of claim 1, wherein the glucokinase activator is administered twice a day.

23. The method of claim 1, further comprising administering a therapeutically effective amount of a second agent to the subject in need thereof.

24. The method of claim 23, wherein the second agent is an antidiabetic agent.

25. The method of claim 23, wherein the second agent is metformin, a dipeptidyl peptidase 4 (DPP-4) inhibitor, a glucagon-like peptide-1 (GLP-1) agonist, an insulin, a meglitinide, a sodium-glucose transport protein 2 (SGLT2) inhibitor, a sulfonylurea, or a thiazolidinedione, or a combination thereof.

26. The method of claim 25, wherein the second agent is a DPP-4 inhibitor.

27. The method of claim 26, wherein the DPP-4 inhibitor is alogliptin, dutogliptin, evogliptin, gemigliptin, gosogliptin, linagliptin, omarigliptin, saxagliptin, sitagliptin, teneligliptin, trelagliptin, or vildagliptin.

28. The method of claim 25, wherein the second agent is an SGLT2 inhibitor.

29. The method of claim 28, wherein the SGLT2 inhibitor is bexagliflozin, canagliflozin, dapagliflozin, empagliflozin, ertugliflozin, ipragliflozin, luseogliflozin, phlorizin, remogliflozin, serglifozin, sotagliflozin, or tofogliflozin.

30. The method of claim 1, wherein the subject is a human.

31. A method of treating or ameliorating one or more symptoms of a chronic kidney disease in a subject, comprising administering to the subject in need thereof a therapeutically effective amount of a glucokinase activator, wherein the glucokinase activator is (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide, or a tautomer, a mixture of two or more tautomers, or an isotopic variant thereof; or a pharmaceutically acceptable salt, solvate, hydrate, or prodrug thereof.

32. The method of claim 31, wherein the chronic kidney disease is a mild chronic kidney disease.

33. The method of claim 31, wherein the chronic kidney disease is a moderate chronic kidney disease.

34. The method of claim 31, wherein the chronic kidney disease is a severe chronic kidney disease.

35. The method of claim 31, wherein the chronic kidney disease is end-stage kidney disease.

36. The method of claim 31, wherein the chronic kidney disease is a diabetic kidney disease.

37. The method of claim 36, wherein the chronic kidney disease is type 1 diabetic kidney disease.

38. The method of claim 36, wherein the chronic kidney disease is type 2 diabetic kidney disease.

39. The method of claim 31, wherein the glucokinase activator is (5)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide.

40. The method of claim 31, wherein the therapeutically effective amount of the glucokinase activator is ranging from about 0.1 to about 50 mg/kg per day or ranging from about 5 to about 1,000 mg per day.

41. The method of claim 31, wherein the therapeutically effective amount of the glucokinase activator is about 75 or about 150 mg per day.

42. The method of claim 31, wherein the glucokinase activator is administered orally.

43. The method of claim 31, wherein the glucokinase activator is administered orally as a tablet.

44. The method of claim 31, wherein the glucokinase activator is administered twice a day.

45. The method of claim 31, wherein the subject is a human.

* * * * *